United States Patent
Fauconet et al.

(10) Patent No.: US 7,622,607 B2
(45) Date of Patent: Nov. 24, 2009

(54) METHOD FOR PURIFYING (METH)ACRYLIC ACID OBTAINED BY OXIDIZING A GASEOUS SUBSTRATE

(75) Inventors: Michel Fauconet, Valmont (FR); Denis Laurent, Saint-Avold (FR)

(73) Assignee: Arkema France, Colombes (FR)

( * ) Notice: Subject to any disclaimer, the term of this patent is extended or adjusted under 35 U.S.C. 154(b) by 456 days.

(21) Appl. No.: 10/577,168

(22) PCT Filed: Oct. 1, 2004

(86) PCT No.: PCT/FR2004/002481
§ 371 (c)(1), (2), (4) Date: Apr. 26, 2006

(87) PCT Pub. No.: WO2005/054171
PCT Pub. Date: Jun. 16, 2005

(65) Prior Publication Data
US 2008/0281124 A1    Nov. 13, 2008

(30) Foreign Application Priority Data
Nov. 4, 2003    (FR) .................................. 03 12906

(51) Int. Cl.
*C07C 51/42* (2006.01)

(52) U.S. Cl. .................................................. 562/600
(58) Field of Classification Search ................ 562/600
See application file for complete search history.

(56) References Cited

U.S. PATENT DOCUMENTS

| 3,868,417 | A | 2/1975 | Duembgen et al. |
| 3,932,500 | A | 1/1976 | Duembgen et al. |
| 5,426,221 | A | 6/1995 | Willersinn |
| 5,780,679 | A | 7/1998 | Egly et al. |
| 6,713,648 | B2 | 3/2004 | Hirao et al. |
| 6,888,025 | B2 | 5/2005 | Hirao et al. |

*Primary Examiner*—Porfirio Nazario Gonzalez
(74) *Attorney, Agent, or Firm*—Steven D. Boyd

(57) ABSTRACT

The present invention relates to a method for purifying (meth) acrylic acid obtained by catalytic or redox oxidation of a gaseous substrate constituting propane, propylene, acrolein, isobutane, isobutene, tert-butyl alcohol and/or (meth)acrolein or mixtures thereof by sending the gaseous reaction mixture to the bottom of a countercurrent absorption column (C1) which is supplied at the top with at least one type of hydrophobic heavy solvent, sending the flow (4) from the bottom of column (C1) to a separation column (C2). Column (C1) is operated at a flow rate of heavy solvent of from 3 to 5.6 times the flow rate of the (meth)acrylic acid in the gaseous reaction mixture and the rectifying column used as a separation column (C2) is operated with the feed at the top and without reflux.

22 Claims, 2 Drawing Sheets

METHOD FOR PURIFYING (METH)ACRYLIC ACID OBTAINED BY OXIDIZING A GASEOUS SUBSTRATE

FIELD OF THE INVENTION

The present invention fits into the context of a method for manufacturing (meth)acrylic acid according to which a gas substrate (propane and/or propylene and/or acrolein in the case of acrylic acid; isobutane and/or isobutene and/or tert-butyl alcohol and/or methacrolein in the case of methacrylic acid) is oxidized by a catalytic or redox method, and the (meth)acrylic acid is recovered from the hot reaction gas mixture, by countercurrent absorption by a solvent.

BACKGROUND OF THE INVENTION

The (meth)acrylic acid absorption methods described use, as an absorption solvent, either water, or an organic solvent, which is usually a hydrophobic compound or a mixture of hydrophobic compounds with a much higher boiling point than that of (meth)acrylic acid.

Absorption methods using water provide an aqueous (meth)acrylic acid solution which requires numerous and costly purification steps to obtain pure (meth)acrylic acid.

On the contrary, absorption methods using hydrophobic organic solvents have the advantage over aqueous methods of reducing the number of purification steps necessary for obtaining pure (meth)acrylic acid. These methods conventionally involve the successive steps of absorption, stripping, removal of light compounds, followed by final distillation of the pure acrylic acid.

The present invention relates to the substantially quantitative recovery (recovery yield>98.5%.), in only three steps of (meth)acrylic acid that is sufficiently stripped of its light impurities to avoid an additional topping step. A second objective of the invention is to achieve this recovery without dilution of the uncondensed waste gas by an external gas added in the stripping step, in order to reduce the size of the column and the loss of unconsumed reactants in the waste gas that must be purged. The third objective is the recovery of pure (meth)acrylic acid without any aqueous pollutant liquid release that is difficult to remove.

The main method for synthesizing acrylic acid uses a reaction of catalytic oxidation of propylene with a mixture containing oxygen. This reaction is generally carried out in the vapor phase, usually in two steps, which may be carried out in two distinct reactors or a single reactor:

the first step carries out the substantially quantitative oxidation of the propylene to an acrolein rich mixture, in which the acrylic acid is a minority component;

the second step completes the conversion of acrolein to acrylic acid.

The gas mixture issuing from the second oxidation step consists of:

acrylic acid;

light compounds incondensable in the temperature and pressure conditions commonly employed (unconverted nitrogen, oxygen and propylene, propane present in the reactive propylene, carbon monoxide and dioxide formed in small quantities by final oxidation);

light condensable compounds, particularly water, generated by the propylene oxidation reaction, unconverted acrolein, light aldehydes, such as formaldehyde and acetaldehyde, and acetic acid, the main impurity generated in the reaction section;

heavy compounds: furfuraldehyde, benzaldehyde, maleic anhydride, etc.

The method for synthesizing (meth)acrylic acid by oxidation is identical in principle to that of acrylic acid, except for the reactive substrate (which may be isobutene or tert-butanol), the intermediate oxidation product (methacrolein) and the types of light condensable byproduct compounds (the reaction gas mixture contains acrylic acid in addition to the light compounds present in the reaction gas of the acrylic acid synthesis method).

The second stage of manufacture consists in recovering the acrylic acid from the hot gas mixture, previously cooled to a temperature of 150-200° C., by introducing this gas at the bottom of an absorption column where it meets a countercurrent flow of solvent introduced at the top of the column, and inside which cooling, condensation, absorption and rectification processes take place simultaneously.

In most of the methods described, the solvent employed in this column is water or a high boiling point hydrophobic solvent.

Regardless of the solvent used, the known methods generally involve:

an absorption column, supplied at the top with solvent, at the bottom of which the reaction gas mixture is introduced, comprising a lower cooling section and in which the gas upflow undergoes partial condensation by meeting a descending liquid mixture stream generally cooled through a heat exchanger, and an upper section designed to absorb the maximum of acrylic acid in the solvent;

a desorption column, supplied with the bottom stream from the absorption column. The role of this column is selectively to remove most of the light compounds absorbed in the preceding step, particularly the acrolein unconverted in the reaction step.

The lighter uncondensed compounds issuing from the reaction gas are removed at the top of the absorption column.

In order to recover part of the unconverted reactants present in this stream, such as propylene and acrolein, in the case of the method for synthesizing acrylic acid, or isobutene and methacrolein in the case of a method for manufacturing methacrylic acid, part of the uncondensed gas stream at the top of the absorption column is generally recycled to the reaction step, the remainder being purged to prevent the holdup of byproducts in the gas loop thus formed.

The maximum proportion of uncondensed gas recycled to the reaction is also limited by economic criteria: since the quantity of gas fed to the reactors is limited by catalyst performance, the (meth)acrylic acid productivity is decreased by dilution of the reactive substrate.

Since (meth)acrylic acid is sensitive to polymerization promoted by high temperatures, the operating temperature in the desorption column is generally limited, either by carrying out this distillation at the temperature of the mixture under reduced pressure, or by introducing an inert gas at the bottom of a stripping column operating under atmospheric pressure or reduced pressure, the two methods serving to decrease the vapor pressure of the condensable compounds, and consequently the temperature of the liquid-gas equilibria governing the separation.

In the case of absorption methods using water as an absorbent solvent, the raw (meth)acrylic acid mixture recovered at the bottom of the desorption column contains a high proportion of water, about 30-50% by weight. Certain polar compounds, which display a strong affinity for this solvent, such as carboxylic acids, are absorbed in the water. This is particularly the case of acetic acid (case of the synthesis of acrylic acid), or of acetic acid and acrylic acid (the case of methacrylic acid synthesis) formed by a side reaction during the reaction step, which passes completely into this raw (meth) acrylic acid stream.

The separation of the majority impurities, that is, water and acetic acid (case of the synthesis of acrylic acid) or water, acetic acid and acrylic acid (case of the synthesis of methacrylic acid), in order to obtain pure acrylic acid or pure methacrylic acid respectively, is difficult. It requires a large number of separation columns. The dehydration step is generally carried out in the presence of a solvent immiscible with water, in an extraction column or heteroazeotropic distillation column, generally coupled with a column for recovery of the solvent partially solubilized in the extracted aqueous phase, in order to recycle it upstream of the method. The step of removal of the light compounds (topping) usually employs one or two columns, and the step of separation of the heavy compounds (tailing) is carried out in a final column, from which the pure (meth)acrylic acid is extracted at the top.

Absorption methods using a nonaqueous solvent have the advantage of reducing the purification steps, particularly by avoiding the use of heavy and costly water separation methods, the use of hydrophobic solvents making it possible to remove the water at the top of the absorption column.

A further advantage of the nonaqueous absorption methods described, over the water absorption method, is to facilitate the removal of the light compounds.

The role of the desorption column located downstream of the absorption column is to reduce the contents of light condensable compounds in the bottom stream of the absorption column, particularly unconverted acrolein, residual water and acetic acid (case of the synthesis of acrylic acid), or methacrolein, water, acrylic acid and acetic acid (case of methacrylic acid).

However, this removal of the light impurities is not complete in the methods described in the prior art. Thus, the method for purifying acrylic acid with absorption by a mixture of diphenyl and diphenyl ether, described in French patent FR-B-2 146 386, yields a raw acrylic acid still containing 0.5% by weight of acetic acid and 0.5% by weight of water. U.S. Pat. No. 5,426,221, describing a method with absorption of acrylic acid by a mixture of diphenyl, diphenyl ether and dimethyl phthalate, serves to improve the removal of water (representing 0.04% by weight of the raw acrylic acid distilled in the example), but it still leaves 0.26% by weight of acetic acid in the purified acrylic acid without an additional topping step. The method of absorption by carboxylic esters described in French patent FR-B-2 196 986 serves to obtain a grade of acrylic acid still containing 0.3% by weight of acetic acid 0.2% by weight of water.

The grades of acrylic acid obtained by this method are insufficient, in the absence of supplementary purification, for the use of the monomer in its conventional applications. To improve the removal of the light compounds without adding an additional column, solutions have been proposed, consisting in carrying out the topping in an upper section added to the final acrylic acid distillation column. Thus, European patent EP-B-706 986 mentions a recovery column in which the acrylic acid is obtained by a side drawoff, the upper section of the column being used to concentrate the residual light compounds at the top, in order to remove them. The major drawback of such a method is the difficulty of separating the light compounds, particularly acetic acid, thereby requiring a significant increase in the number of trays of the column and condensed flow rate returned to the top (reflux) to ensure the separation and reduce the loss of acrylic acid. This causes a substantial increase in the size of the column, and hence in the investment cost, where, at equivalent column size, a decrease in the column distillation capacity. Furthermore, this system generates a stream still containing AA which, to avoid its loss, must be recycled to a preceding step. This makes the method even more complex and limits the capacity of the column receiving this stream.

A further drawback of absorption methods using heavy hydrophobic solvents is the fact that large quantities of solvent are needed to absorb all the acrylic acid present in the reaction gases. In French patent FR-B-2 146 386, to reach a sufficient recovery rate and avoid costly losses of unabsorbed acrylic acid, the mass ratio of solvent (mixture of diphenyl and diphenyl ether) to acrylic acid is about 9/1, or a concentration of acrylic acid in the raw mixture after absorption and desorption, of about 10%. The consequences of the large size of the columns and ancillary equipment and storage units, higher energy costs associated with vaporization of high boiling point solvent in the columns.

Moreover, the absorption methods using nonaqueous solvents described in the literature have the common feature of carrying out the desorption step by stripping by an inert gas introduced at the bottom of the column. This inert gas may be nitrogen, air or part or all of the uncondensed gases at the top of the absorption column. The quantity introduced generally represents between 15% and 30% of the total gas input issuing from the reaction step. The drawback of this introduction of external gas is that, being sent to the absorption column to recover the acrylic acid that it contains, is added to the reaction gas which makes up its main feed, and consequently, the maximum absorption capacity of the column is thereby limited. Finally, and for equivalent at production capacity, the size of the absorption and stripping columns increases with the flow rate of external gas introduced.

A further drawback of the method of stripping by an external gas is to dilute the uncondensed gases at the top of the column and consequently cause a dilution of the part of these gases sent to the reaction step in order to recover the noble compounds that they contain (propylene, acrolein, traces of acrylic acid). Thus, for the same quantity of noble compounds recycled in the absence of external stripping gas, the flow of gases entering the reactor is increased by the introduction of this external gas. This results either in an increase in the flow rate of gas fed to the reactors, at constant reactant flow rate, causing accelerated aging of the catalysts due to the higher operating temperature to obtain the same yield performance, or, at constant flow rate of gas entering the reactors, reduced productivity by decreasing the flow rate of the reactants.

European patent EP 706 986, which describes a method of absorption by nonaqueous solvent without a desorption column, is incapable of obtaining the efficient removal of the light compounds, particularly acetic acid, claimed in the methods described with a desorption column.

Finally, the patents described in the prior art mention a water condensation section at the top of the absorption column. The condensed aqueous stream is particularly rich in polar compounds having volatilities lower than or close to that of water, particularly organic acids such as formic acid, acetic acid and acrylic acid. Due to the pollutant nature of this stream, it cannot be removed without subsequent removal treatment, generally by incineration of the organic compounds. The cost of this incineration treatment is increased by the fact that the stream to be treated is a liquid stream, consisting mainly of water.

European Patent Application EP-A2-1 125 912 teaches a method for purifying acrylic acid comprising a step of absorption by a heavy hydrophobic solvent, followed by a distillation step in a column under reduced pressure for topping, followed by distillation to obtain the acrylic acid without the solvent.

According to this method, the mass flow rate of heavy solvent is 0.2-4.5 times the mass flow rate of acrylic acid, and the stream sent to the column under reduced pressure contains acrylic acid at the rate of 18 to 75% by weight.

SUMMARY OF THE INVENTION

The applicant company has tried to further improve the absorption efficiency and decrease the proportion of acetic acid in the acrylic acid.

This purpose has been achieved by the choice of a particular range of the solvent/(meth)acrylic acid ratio and by carrying out the desorption step using a rectification column that is distinguished from the distillation column of European Application EP-A2-1 125 912 by the fact that it operates with a top feed, without reflux, and by particular operating conditions of this column, such as its distillate rate relative to the flow rate of (meth)acrylic acid introduced into the absorption column.

In the method according to European Patent Application EP-A2-1 125 912, the two absorption and distillation columns are independent. Due to its operation with the high imposed reflux ratio (preferably 3/1 to 6/1), the distillate rate of the distillation column sent to the absorption column, relative to the rate of flow of acrylic acid flowing into the latter column, is very low (<0.1/1). On the contrary, according to the present invention, the two columns of absorption and rectification without reflux, form an inseparable whole, the performance of one being dependent on that of the other, and the composition of the stream of the loop flowing between the bottom of C1 and the top of C2 serves to improve the overall separation performance.

Surprisingly, the overall performance is improved in relation to the method according to EP-A2-1 125 912 despite the lower column efficiencies: the absorption column has been estimated at 65-70 theoretical trays in the examples of the abovementioned patent application, compared with 35-40 in the examples of the invention; and the distillation column has 28 Oldershaw trays in the examples of the abovementioned European Patent Application, compared with 15 perforated downcomer-type trays with equivalent theoretical efficiency in the examples of the present invention.

Furthermore, the use of a rectification column without reflux, supplied at the top, has the advantage, over a rectification column with reflux, of significantly reducing the formation of polymers at the top of the column, the (meth)acrylic acid concentration in the liquid present on the upper trays being much lower than in a rectification column.

DETAILED DESCRIPTION OF THE INVENTION

Figure 1:
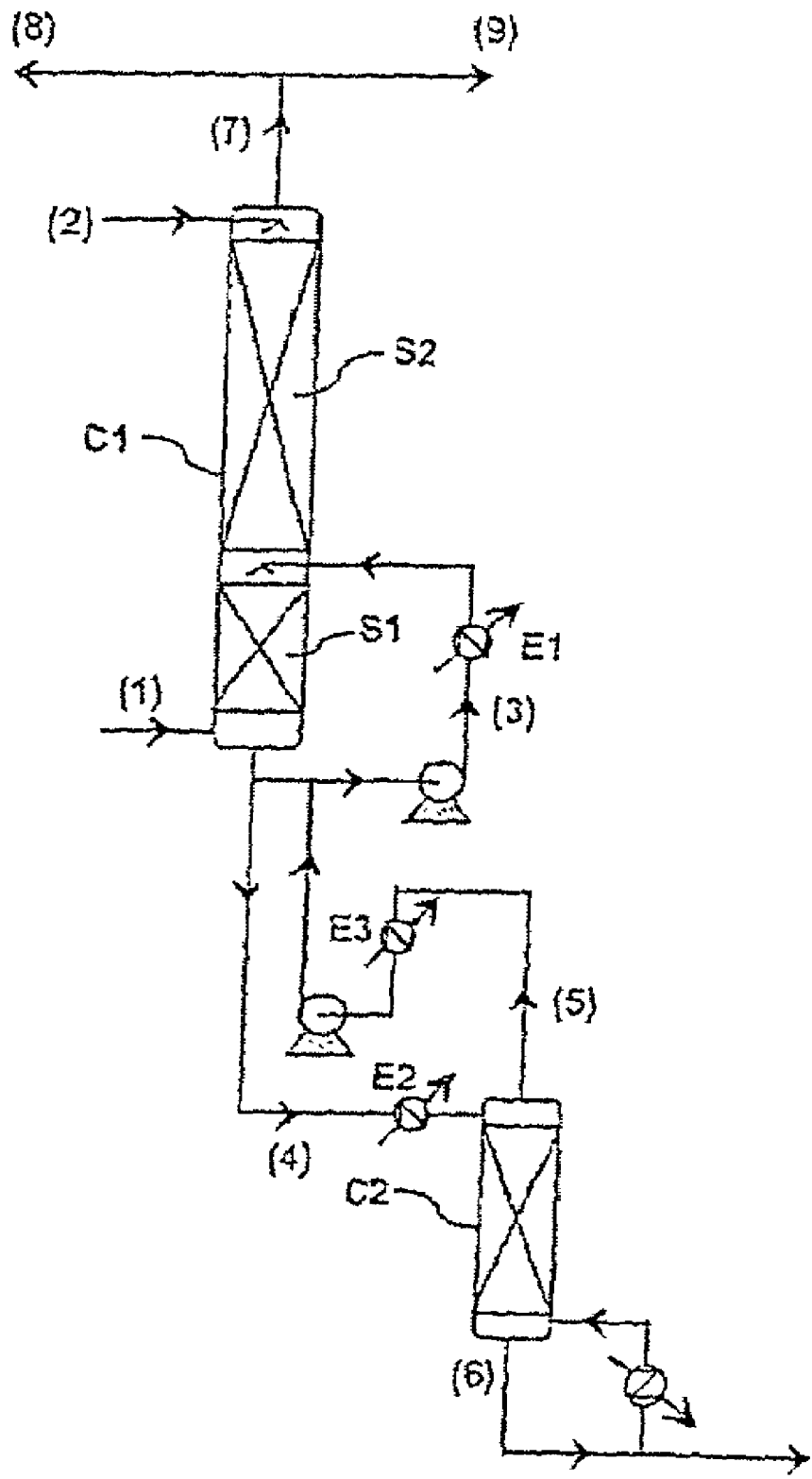
FIG. 1 is a schematic flow sheet of a preferred embodiment of the invention.

The method in the present invention is suitable, with only two columns (one absorption column, one rectification column) for carrying out simultaneously:
  the recovery of (meth)acrylic acid with a yield higher than 98.5%, advantageously higher than 99%;
  the recovery of a stream of raw (meth)acrylic acid concentrated in the solvent, containing at least 20% of (meth)acrylic acid;
  the nearly complete removal of the light compounds, particularly water and acetic acid (case of the synthesis of acrylic acid) or water, acetic acid and acrylic acid (case of the synthesis of methacrylic acid), making it possible, without an additional topping step, to obtain a (meth)acrylic acid advantageously containing less than 0.05% of water, less than 0.01% of acrolein and less than 0.1% of acetic acid.

The percentage of (meth)acrylic acid obtained in the bottom of the rectification column is substantially 10-33% by weight, particularly 20% to 25% by weight.

Moreover, since the rectification step is carried out without the introduction of external inert gas, the method described has the additional advantage of reducing the size of the purification equipment and facilitating the recycling of the uncondensed gases at the top of the absorption column to the reaction step.

Finally, according to a particularly advantageous embodiment, the uncondensed gas at the top of the absorption column undergoes no condensation, and is sent in gaseous form, partly to the reaction step and partly to a purge treatment section (incineration). This results in a substantial decrease in pollutant aqueous releases and in the cost of the treatment of the purge stream.

Thus the subject of the present invention is a method for purifying (meth)acrylic acid obtained by catalytic or redox oxidation, of a gas substrate consisting of propane and/or propylene and/or acrolein in the case of the manufacture of acrylic acid, and of isobutane and/or isobutene and/or tert-butyl alcohol and/or methacrolein in the case of the manufacture of methacrylic acid, said gas mixture (1) mainly consisting of:
  propane and/or propylene or isobutane and/or isobutene if previously contained by the substrate;
  final oxidation products;
  the desired (meth)acrylic acid;
  (meth)acrolein;
  tertbutyl alcohol in the case of the manufacture of methacrylic acid;
  water vapor;
  acetic acid with, in the case of the manufacture of methacrylic acid, acrylic acid as a byproduct; and
  heavy products of side reactions, according to which the reaction gas mixture (1) is sent to the bottom of an absorption column (C1) which is supplied at the top and in countercurrent with at least one heavy hydrophobic absorption solvent, to obtain:
  at the top of the column (C1) a gas stream (7) consisting of:
  propane and/or propylene or isobutane and/or isobutene, according to whether acrylic acid or methacrylic acid is manufactured, and the products of the final oxidation of the mixture (1);
  major quantities of water and acetic acid in the case of the manufacture of acrylic acid, or of water, acetic acid and acrylic acid in the case of the manufacture of methacrylic acid; and
  (meth)acrolein;
  at the bottom of said column (C1), a stream (4) consisting of:
  (meth)acrylic acid;
  the heavy absorption solvent or solvents;
  the heavy products of side reactions; and
  minor quantities of acetic acid and water, in the case of the manufacture of acrylic acid and acetic acid, acrylic acid and water in the case of the manufacture of methacrylic acid, the stream issuing from the column (C1) is then sent to a separation column (C2) in which a separation is carried out to obtain:

at the top, a stream consisting of light impurities which are sent to the bottom part of the absorption column (C1); and at the bottom, a stream consisting of:

(meth)acrylic acid in solution in the absorption solvent or solvents;

a small proportion of acetic acid in the case of the manufacture of acrylic acid and acetic acid and of acrylic acid in the case of the manufacture of methacrylic acid;

the heavy products of side reactions; and the polymerization inhibitor or inhibitors, characterized in that the column (C1) is operated with a heavy solvent flow rate that is 3 to 5.6 times the flow rate of (meth)acrylic acid in the feed gas mixture, and in that, as a separation column (C2), a rectification column is used, which is operated with a flow feed and without reflux.

According to an advantageous feature of the method of the invention, the column (C2) is operated under conditions such that its distillate rate relative to the flow rate of (meth)acrylic acid introduced into the absorption column (C1) is between 0.5/1 and 4/1, particularly between 2/1 and 3/1.

An absorption column (C1) is advantageously used comprising:

in its lower part, at least one cooling section (S1) equipped with a system for recirculating, via an external heat exchanger (E1), part of the stream collected in the lower part of said section or sections (S1) to send it to the flow of said sections; and in its upper part, a section (S2) for the absorption and rectification of the reaction gas mixture.

A section (S2) in particular is used, in which the number of theoretical plates is 25 to 50, and preferably 30 to 45.

The absorption is carried out in the column (C1) generally at atmospheric pressure or under a pressure close to atmospheric pressure, and advantageously at a solvent introduction temperature of 20 to 80° C., preferably 30 to 60° C.

According to particular features of the method of the invention, the column (C1) is operated at a bottom temperature of 50 to 120° C., particularly of 70 to 100° C.; at a overhead head gas temperature of 40 to 70° C., particularly of 50 to 60° C.; and the reaction gases are introduced at a temperature of 100° C. to 200° C., particularly of 130° C. to 180° C.

The patent literature provides numerous examples of heavy hydrophobic solvents. Advantageous use is made of one or more heavy hydrophobic absorption solvents having a boiling point above 200° C. under atmospheric pressure, ditolylether being particularly preferred as a heavy hydrophobic solvent. The absorption column (C1) can be fed with one or more pure solvents and/or with one or more solvents issuing from the recycling of one or more streams obtained from the subsequent purification steps.

The absorption is generally carried out in the column (C1) in the presence of at least one polymerization inhibitor, selected in particular from phenolic derivatives such as hydroquinone and its derivatives such as methyl ether of hydroquinone, phenothiazine and its derivatives, such as methylene blue, quinones, such as benzoquinone, metal thiocarbamates, such as copper dibutyldithiocarbamate, compounds with nitroso groups, such as N-nitroso-phenylhydroxylamine, amines such as derivatives of paraphenylenediamine, or N-oxyl compounds, such as 4-hydroxy-2,2,6,6-tetramethyl-piperidine-N-oxyl.

According to a first embodiment of the method of the invention, the gas stream issuing from the top of the column (C1) is removed partly to the reaction section, and partly to an incineration or purge step.

According to a second embodiment of the method of the invention, the gas stream issuing from the top of the column (C1) is sent to the bottom of a condensation section (S3) where this gas mixture is placed in intimate contact with a descending liquid stream fed at the top of said section (S3) and consisting of the recycling of part of the bottom stream of said section (S3) previously cooled by an external heat exchanger (E4).

Figure 2:
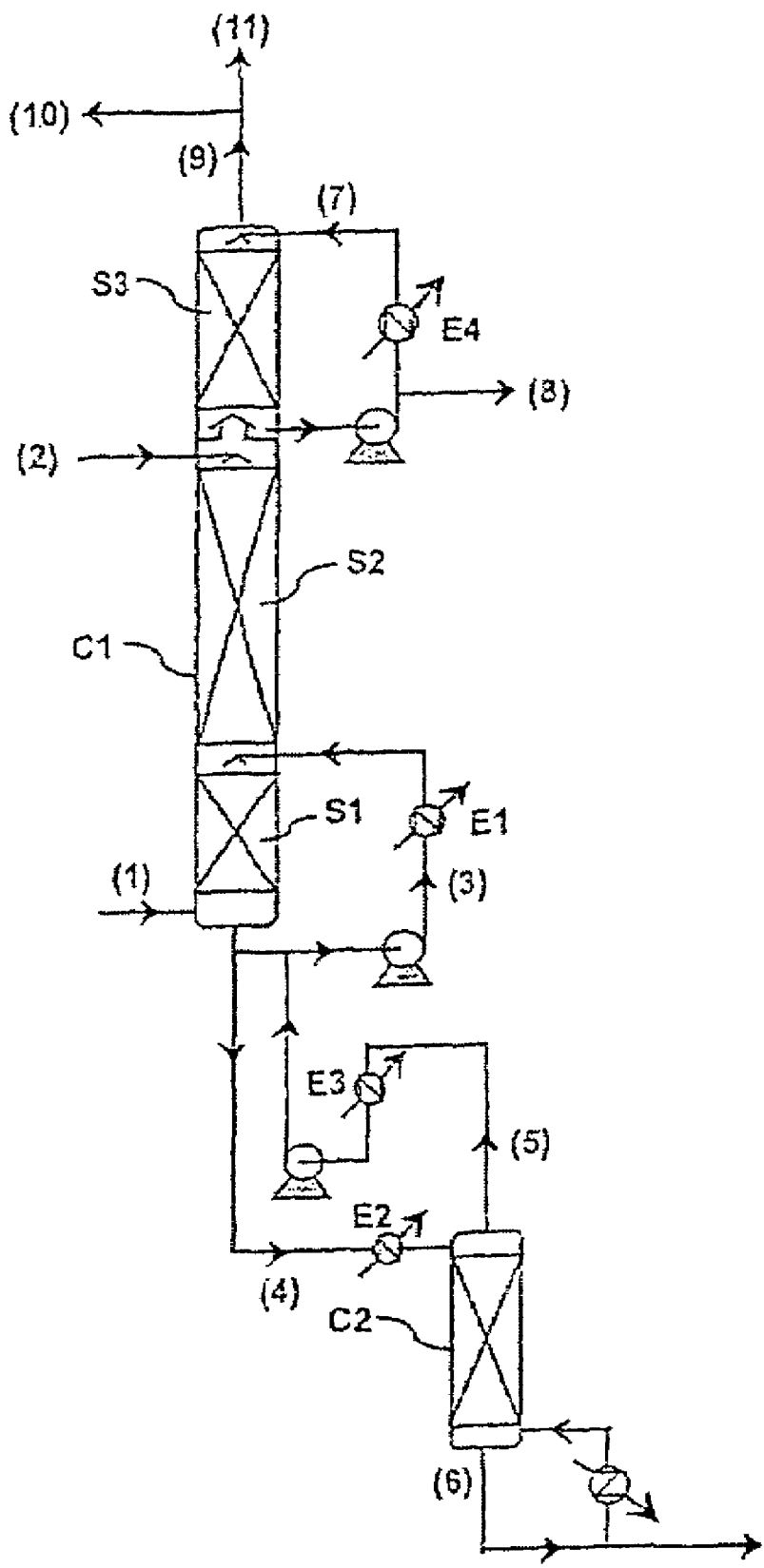
FIG. 2 is schematic flow sheet of an alternate embodiment of the invention.

The diagrams appended hereto illustrate the invention (FIGS. 1 and 2).

FIG. 1 shows a first embodiment. The reaction gas mixture issuing from the oxidation of propylene and acrolein (in the case of the manufacture of acrylic acid) or from the oxidation of isobutene and methacrolein (in the case of the manufacture of methacrylic acid), mainly consists of:

on the one hand, incondensable compounds in the operating pressure conditions of the column: propylene, final oxidation products ($CO$, $CO_2$);

on the other, condensable compounds: acrylic acid, acrolein, water and acetic acid in the case of the manufacture of acrylic acid, or methacrylic acid, methacrolein, water, acrylic acid and acetic acid in the case of the manufacture of methacrylic acid, heavier side reaction products in very small quantities, is sent (stream 1) to the bottom of an absorption column C1 fed at the top and in countercurrent with a solvent (stream 2: heavy hydrophobic solvent with a boiling point above 200° C. under atmospheric pressure).

Preferably, the column comprises:

in its lower part, one or more cooling sections S1 equipped with systems for recirculating, through one or more external heat exchangers E1, part of the stream collected in the lower part of S1 (stream 3), to send it to the top of this section;

in its upper part, a section S2 in which the absorption and rectification of the mixture is carried out.

The solvent feed is provided above the section S2. The solvent introduced may be a pure solvent or may issue from a recycling of a stream obtained in the subsequent purification steps. Preferably, the column C1 operates under a pressure close to atmospheric pressure.

The stream 4 obtained at the bottom of the column C1 mainly consists of acrylic acid and solvent, and small quantities of acetic acid, water and acrolein. This stream 4, of which the temperature may optionally be adjusted through a heat exchanger E2, is then stripped of these light impurities (desorption step) by sending it to the top of a distillation column C2 in which they are concentrated at the top, in a mixture with acrylic acid and traces of solvent. The gas stream 5 is condensed through a heat exchanger E3 and sent to the column C1, at a place located in the lower part thereof, preferably in one of the cooling loops S1. The stream 6 obtained at the bottom of column C2 then mainly consists of acrylic acid in solution in the solvent, and heavy impurities, issuing from side reactions, present in small quantities in the reaction gas stream.

Advantageously, the column C2 operates under reduced pressure and the gas used for the desorption of the light compounds is generated by boiling the column bottom mixture through a heat exchanger (boiler).

The gas stream 7 issuing from the column C1 contains the compounds initially present in the reaction gas and not absorbed: incondensable products at the operating pressure of the column (propylene, CO, $CO_2$ in the case of the manufacture of acrylic acid; isobutene, CO, $CO_2$, in the case of the manufacture of methacrylic acid), water, acrolein or methacrolein according to whether acrylic acid or methacrylic acid is manufactured, acetic acid in the case of the manufacture of acrylic acid, or acetic acid and acrylic acid in the case of the manufacture of methacrylic acid.

According to the first embodiment (FIG. 1), the gas stream 7 issuing from the top of the column C1 contains all the water, formic acid, acetic acid and acrolein, which are directly removed, partly to the reaction section (stream 8), to complete the conversion of the noble reactants that it contains, and partly (stream 9) to an incineration (purge) treatment step.

According to a second embodiment (FIG. 2), the ascending gas stream issuing from the section S2 of column C1 is sent to the bottom of a condensation section S3 where this gas mixture is placed in intimate contact with a descending liquid stream (stream 7), fed at the top of this section, and consisting of the recycling of part of the bottom stream from section S3 previously cooled by a heat exchanger E4.

The section S3 may also consist of a distinct column in series with the column C1. The gas stream 9 from the top of section S3 contains the compounds present in the gas stream issuing from the top of section S2, except part of the water and all the formic acid, acetic acid (case of the manufacture of acrylic acid) or acetic acid and acrylic acids (case of the manufacture of methacrylic acid), which are removed in the stream 8. Most of the stream 9 will be advantageously recycled to the reaction step (stream 10), to convert the noble reactants which it contains, and a slight purge of this stream (stream 11) can be carried out to prevent holdup in the loop thus formed of the incondensable compounds resulting from the final oxidation of the propylene (CO, $CO_2$) and the nitrogen from the air introduced in the reaction step.

EXAMPLES

In these Examples, the following abbreviations have been used:
AA: acrylic acid;
AcOH: acetic acid;
ACO: acrolein;
DTE: ditolylether;
EMHQ: hydroquinone methyl ether The examples described below illustrate the invention. The percentages are indicated as mass percentages.

Example 1

The experimental rig used is the one shown in FIG. 1 in the drawing appended hereto.

The gas mixture fed to the absorption column C1 is representative of a reaction medium issuing from the second stage of a reactor for oxidizing propylene to acrylic acid. It consists of condensable compounds:
AA: 14.1%;
AcOH: 0.8%;
ACO: 0.45%;
$H_2O$: 7.81% and incondensable inert compounds:
$N_2$: 69.83%;
$O_2$: 2.5%;
propylene: 1.2%;
$CO_2$: 3.31%.

This gas mixture is sent at a rate of 709 g/h, at a temperature of 165° C., to the bottom of a glass column C1, having an overall efficiency of 42 theoretical trays, and consisting of a lower cooling section S1 equipped with five perforated trays with downcomer, and an upper absorption-distillation section S2 equipped with 14 Sulzer type packing elements EX. The reaction gas is fed at the bottom of the lower cooling section S1.

The column C1 is fed at the top of its upper section S2 with a stream consisting of DTE, at a flow rate of 400 g/h (solvent/acrylic acid ratio in the reaction gas=4/1), in which 0.1% of EMHQ has been previously dissolved as polymerization inhibitor. The temperature of introduction of the absorption solvent is 54° C.

The operating pressure in the column C1 is atmospheric pressure. The temperature measured at the bottom of the column C1 is 84° C. The temperature is 52° C. at the top of this column C1.

To analyze all the organic compounds entrained in the flow gas stream, it is absorbed in a scrubbing column where it meets a large countercurrent stream of water (13 700 g/h) at a temperature of 20° C.

The acetic acid recovered at the top represents 98.7% of initial acetic acid, and acrylic acid, 0.3% of the initial acrylic acid (acrylic acid recovery yield: 99.7%).

Part of the liquid stream obtained at the bottom of section S1 of the absorption column C1 is sent via a pump through a double jacket heat exchanger E1, where it is cooled to 70° C., at the top of section S1.

The remainder of the mixture obtained at the bottom of section S1 is cooled through a heat exchanger E2, to a temperature of 35° C., and is then sent via a pump to the top of a glass column C2, equipped with 15 perforated trays with downcomer, for a total efficiency of 11 theoretical trays. The column C2 is provided at the bottom with a thermosiphon boiler and at the top of a condenser E3.

The distillation is carried out in this column C2 under reduced pressure of 187 hPa (140 mmHg). The temperature measured at the bottom of column C2 is 113° C., and the temperature at the top reaches 88° C.

All the vapors condensed in the heat exchanger E3 (318 g/h, or a mass ratio of distillate rate relative to the flow rate of acrylic acid introduced into the column C1 of 3.2/1) is sent via a pump to the external cooling loop of the column C1, upstream of the pump which recirculates the bottom mixture of section S1, through the heat exchanger E1, to the top of the section.

The liquid stream extracted at the bottom of this column C2 (497.6 g/h), contains 20.2% of acrylic acid. After distillation to separate the solvent, the acrylic acid obtained at the top of the column contains 0.068% of acetic acid, less than 0.01% of acrolein and less than 0.01% of water.

Example 2

The experimental rig is identical to that of the preceding Example 1.

The column C1 operates under atmospheric pressure, while the operating pressure of the column C2 is 187 hPa (140 mmHg).

A gas mixture with the same composition is fed with the same flow rate to column C1 in its lower part, at a temperature of 165° C.

The flow rate of DTE introduced at a temperature of 53° C. at the top of column C1 is now reduced to 300 g/h (solvent/acrylic acid ratio in the reaction gas=3/1).

The column top temperature is 51° C., and the bottom temperature is 77° C. The top and bottom temperatures for column C2 are 83° C. and 111° C. respectively. Part of the bottom stream of column C1 sent to the top of section S1 is cooled to 68° C. through the heat exchanger E1. The remainder of the liquid stream from the bottom of column C1 fed to the column C2 is previously cooled to 34° C. The mass ratio of the distillate rate of the column C2 relative to the flow rate of acrylic acid fed to the column C1 is 3.3/1.

The acetic acid and acrylic acid recovered after absorption of the water stripping column (17 600 g/h) respectively represent 98.6% and 0.9% of the initial compounds (acrylic acid recovery yield: 99.1%).

The acrylic acid concentration in the bottom stream of column C2 reaches 24.5%. After separating the solvent by distillation, the acrylic acid obtained only contains 0.087% of acetic acid and less than 0.01% of acrolein and water.

Example 3

In the same conditions of experimental rig, pressure, temperature, composition and input gas flow rate as in Example 1, the acrylic acid is absorbed by a countercurrent stream on DTE fed at the top of the column at a flow rate of 560 g/h (solvent/acrylic acid ratio in the reaction gas: 5.6/1) and at a temperature of 50° C.

The column flow temperature is 51.6° C., and the bottom temperature is 82° C. The flow and bottom temperatures of column C2 are 86.4° C. and 120.5° C. respectively. The part of the stream of column C1 sent to the top of section S1 is cooled to 69° C. through the heat exchanger E1. The remainder of the bottom liquid stream of column C1 is fed to column C2 at a temperature of 61° C. The mass ratio of the distillate rate of column C2 relative to the flow rate of acrylic acid fed to the column C1 is 1.1/1.

The stream obtained at the bottom of column C2 contains 15.1% of acrylic acid. After separating the solvent by distillation, the acetic acid concentration in the acrylic acid obtained is 0.058%, and this stream contains less than 0.01% of acrolein and water.

The acetic acid and acrylic acid recovered after absorption in the water stripping column (21 120 g/h) represent 99.55% and 0.4% of the initial compounds (acrylic acid recovery yield: 99.6%).

Example 4 (Comparative)

In the same conditions of experimental rig, pressure, temperature, composition and input gas flow rate as in Example 1, the acrylic acid is absorbed by a countercurrent stream DTE fed at the top of the column at a flow rate of 100 g/h (solvent/acrylic acid ratio in the reaction gas=1/1) and a temperature of 45° C.

The column flow temperature is 52.6° C., and the bottom temperature is 78.9° C. The top and bottom temperatures of column C2 are 84.9° C. and 104.4° C. respectively. The part of the stream of column C1 sent to the top of section S1 is cooled to 70° C. through the heat exchanger E1. The remainder of the bottom liquid stream of column C1 is fed to column C2 at a temperature of 74° C. The mass ratio of the distillate rate of column C2 relative to the flow rate of acrylic acid fed to the column C1 is 3.9/1.

The stream obtained at the bottom of column C2 contains 44.6% of acrylic acid. After separating the solvent by distillation the acetic acid concentration in the acrylic acid obtained is 0.045%, and this stream contains less than 0.01% of acrolein and water.

The acetic acid and acrylic acid recovered after absorption in the water stripping column (19 550 g/h) represent 99.35% and 17.2% of the initial compounds. The acrylic acid recovery yield is therefore particularly low: 82.2%.

To try to improve this recovery yield, the experiment was repeated in identical conditions, apart from the fact that the column C1 contained three additional SULZER EX elements in its section S2. The total efficiency of the column was then 50 theoretical trays.

On completion of the test, the performance was not significantly improved: acetic acid concentration in the distilled acrylic acid: 0.054%, and acrylic acid recovery yield: 84%.

A third attempt to improve the acrylic acid recovery yield, in the same conditions as described above, but reducing the solvent feed temperature of the top of the column C1 to 20° C., also terminated in failure. In the operating conditions under atmospheric pressure of the absorption column, the removal of the light compounds of the top of the column became impossible, thereby causing the holdup of these light compounds of the column bottom, the flooding of the column C2 and the rapid formation of polymers in this latter column.

Example 5 (Comparative)

This example is carried out in the same conditions of pressure, temperature, composition and flow rate of input gas as in Example 1. The rig is the same as in Example 1, apart from the fact that the absorption column was equipped with 17 SULZER EX elements in section S2, equivalent to a total efficiency of the column C1 of 50 theoretical trays. The acrylic acid was absorbed by a countercurrent stream of ditolylether fed at the top of the column at a flow rate of 233 g/h (solvent/acrylic acid ratio in the reaction gas=2.33/1) and a temperature of 45° C.

The column C1 flow temperature is 51.5° C., and the bottom temperature is 76.9° C. The flow and bottom temperatures of column C2 are 83.3° C. and 108.5° C. respectively. The part of the stream of column C1 bottom sent to the top of section S1 is cooled to 75° C. through the heat exchanger E1. The remainder of the bottom liquid stream of column C1 is fed to column C2 at a temperature of 35° C. The mass ratio of the distillate rate of column C2 relative to the flow rate of acrylic acid fed to the column C1 is 3/1.

The stream obtained at the bottom of column C1 contains 29.5% of acrylic acid. After separating the solvent by distillation the acetic acid concentration in the acrylic acid obtained is 0.06%, and this stream contains less than 0.01% of acrolein and water.

The acetic acid and acrylic acid recovered after absorption in the water stripping column (18 540 g/h) respectively represent 99.04% and 3% of the initial compounds. The acrylic acid recovery yield therefore remains low: 97%, despite the increased efficiency of the column C1.

Example 6

The principle of the method employed in this third example is that of FIG. 2 appended hereto. The columns C1 and C2 are identical, operating at the same pressures as in the preceding examples, and an additional partial condensation column C3 (equivalent to the section S3 in FIG. 2), operating at atmospheric pressure, is placed in a series at the top of the column C1, in order to remove the organic compounds entrained in the top gas stream of this column, in the form of an aqueous stream.

The reaction gas mixture (709 g/h) of the same composition as in the preceding examples is introduced at a temperature of 164° C. into column C1. The DTE is fed to this column C1 at the top, at a rate of 300 g/h, at a temperature of 53° C. The respective temperatures at the top and bottom of column C1 are 51° C. and 77° C., those of column C2 are 83° C. (flow) and 111° C. (bottom) The bottom stream of column C1 in the recirculation loop at the top of section S1 is cooled to 68° C. through the heat exchanger E1. The remainder of this bottom stream of column C1 is fed to column C2 at a temperature of 32° C. The mass ratio of the distillate rate of the column C2 relative to the flow rate of acrylic acid fed to the column C1 is 1.9/1.

The liquid stream obtained at the bottom of column C2 (raw acrylic acid) contains 24.5% of acrylic acid. After distillation to remove the solvent, the pure acrylic acid obtained contains 0.08% of acetic acid, less than 0.01% of water and less than 0.01% of acrolein.

The gas stream extracted from the top of column C2 is sent to the bottom of the condensation column C3, where it encounters an aqueous countercurrent stream formed by the recirculation, to the top of column S3, and through a heat exchanger E4, of part of the stream recovered at the bottom of this column. The temperature of the uncondensed gases at the top of this section is 42° C. A purge of 22.3 g/h (or 35% of the water present in the initial reaction gas) is carried out at the recirculation loop of this column. This purged aqueous mixture contains 11.24% of acetic acid (or 49% of the initial acetic acid) and 0.08% of acrolein (or 0.56% of the initial acrolein).

The gas stream leaving the top of the condensation column is sent in countercurrent with a high flow of water (18 250 g/h) in a stripping column intended to quantify the losses of organic products in the uncondensed stream at the top of S3. All the acetic acid and the acrylic acid recovered at the top of column C2 (condensation column and stripping column) respectively represents 98.5% and 0.9% of the compounds present in the initial reaction gas (acrylic acid recovery yield: 99.1%).

The invention claimed is:

1. A process for the purification of (meth)acrylic acid from reaction gas mixture obtained by catalytic or redox oxidation of a gas selected from the group consisting of propane, propylene, acrolein, isobutane, isobutene, tertbutyl alcohol, (meth)acrolein and mixture thereof, characterized in that:
    said purification takes place in the presence of at least one polymerization inhibitor;
    said reaction gas mixture (1) is sent to the bottom of an absorption column (Cl) which is supplied at the top and in countercurrent flow with at least one heavy hydrophobic absorption solvent or solvents, to obtain:
    at the top of the column (Cl) a gas stream (7) consisting of propane, propylene, isobutane, isobutene, the products of the final oxidation of the reaction gas mixture (1), major quantities of water, acetic acid, acrylic acid, acrolein and mixtures thereof;
    at the bottom of said column (C1), a stream (4) consisting of (meth)acrylic acid, said at least one heavy absorption solvent or solvents, minor quantities of acetic acid, water, acrylic acid and mixtures thereof;
    the stream (4) issuing from the bottom of column (Cl) is sent to a separation column (C2) in which a separation is carried out to obtain:
    at the top of column (C2), a stream (5) consisting of light impurities which are sent to the bottom of absorption column (Cl); and
    at the bottom, a stream (6) consisting of components selected from the group consisting of (meth)acrylic acid in solution in the at least one heavy absorption solvent or solvents, a small proportion of acetic acid, acrylic acid, polymerization inhibitor or inhibitors and mixtures thereof characterized in that column (Cl) is operated with flow rate of said at least one heavy hydrophobic absorption solvent or solvents that is 3 to 5.6 times the flow rate of (meth)acrylic acid in the reaction gas mixture, and in that, as a separation column (C2), a rectification column is used, which is operated with a top feed and without reflux and without the introduction of external inert gas.

2. The method as claimed in claim 1, characterized in that the column (C2) is operated under conditions such that its distillate rate relative to the flow rate of (meth)acrylic acid introduced into the absorption column (Cl) is between 0.5/1 and 4/1.

3. The method as claimed in claim 2, characterized in that the column (C2) is operated under conditions such that its distillate rate relative to the flow rate of (meth)acrylic acid introduced into the absorption column (Cl) is between 2/1 and 3/1.

4. The method as claimed in claim 1, characterized in that the column (C1) is operated with a flow rate of said at least one heavy hydrophobic absorption solvent that is 3 to 4 times the flow rate of (meth)acrylic acid in the reaction gas mixture.

5. The method as claimed in claim 1, characterized in that an absorption column (C1) is used comprising:
    in its lower part, at least one cooling section (S1) equipped with a system for recirculating, via an external heat exchanger (E1), part (3) of the stream (4) collected in the lower part of said at least one cooling section (S1) to send it to the flow of said section; and
    in its upper part, a section (S2) for the absorption and rectification of said reaction gas mixture (1).

6. The method as claimed in claim 5, characterized in that a section (S2) is used, in which the number of theoretical plates is 25 to 50.

7. The method as claimed in claim 1, characterized in that the absorption is carried out in the column (C1) at atmospheric pressure or under a pressure close to atmospheric pressure, and at a solvent introduction temperature of 20 to 80° C.

8. The method as claimed in claim 1, characterized in that the column (C1) is operated at a bottom temperature of 50 to 120° C.

9. The method as claimed in claim 1, characterized in that the column (C1) is operated at a overhead gas temperature of 40 to 70° C.

10. The method as claimed in claim 1, characterized in that the reaction gas mixture is introduced at a temperature of 100° C. to 200° C.

11. The method as claimed in claim 1, characterized in that one or more heavy hydrophobic absorption solvents are used, having a boiling point above 200° C. at atmospheric pressure.

12. The method as claimed in claim 11, characterized in that ditolylether is used as a heavy hydrophobic solvent.

13. The method as claimed in claim 1, characterized in that the absorption column (C1) is fed solvent selected from one or more pure solvents, solvents issuing from the recycling of one or more streams obtained from the subsequent purification steps.

14. The method as claimed in claim 1, characterized in that the absorption is carried out in the column (C1) in the presence of at least one polymerization inhibitor, selected from phenolic derivatives, phenothiazine and its derivatives, quinones, metal thiocarbamates, compounds with nitroso groups, amines, or N-oxyl compounds.

15. The method as claimed in claim 1, characterized in that the gas stream (7) issuing from the top of the column (C1) is removed, partly to the reaction section, and partly to an incineration or purge step.

16. The method as claimed in claim 1, characterized in that the gas stream (7) issuing from the top of the column (C1) is sent to the bottom of a condensation section (S3) where said gas stream (7) is placed in intimate contact with a descending liquid stream (7') supplied at the flow of said section (S3) and consisting of the recycling of part of the bottom stream of said section (S3) previously cooled by an external heat exchanger (E4).

17. The method as claimed in claim 5, characterized in that a section (S2) is used, in which the number of theoretical plates is 30 to 45.

18. The method as claimed in claim 1, characterized in that the absorption is carried out in the column (C1) at atmospheric pressure or under a pressure close to atmospheric pressure, and at a solvent introduction temperature of 30 to 60° C.

19. The method as claimed in claim 1, characterized in that the column (C1) is operated at a bottom temperature of 70 to 100° C.

20. The method as claimed in claim 1, characterized in that the column (C1) is operated at a overhead gas temperature of 50 to 60° C.

21. The method as claimed in claim 1, characterized in that the reaction gas mixture is introduced at a temperature of 130° C. to 18° C.

22. The method as claimed in claim 1, characterized in that the absorption is carried out in the column (C1) in the presence of at least one polymerization inhibitor, selected from hydroquinone and its derivatives such as methyl ether of hydroquinone, methylene blue, benzoquinone, copper dibutyldithiocarbamate, N-nitroso-phenylhydroxylamine, derivatives of paraphenylenediamine, or 4-hydroxy-2,2,6,6-tetramethylpiperidine-N-oxyl.

* * * * *